(12) United States Patent
Alshehri et al.

(10) Patent No.: US 12,404,222 B2
(45) Date of Patent: *Sep. 2, 2025

(54) SYSTEMS AND METHODS FOR ENHANCING THE EXTRACTIVE SECTION OPERABILITY AND MODIFYING SOLVENT HEAT RECOVERY CYCLE IN THE SEPARATION OF C4 MIXTURES

(71) Applicant: SABIC Global Technologies B.V., Bergen op Zoom (NL)

(72) Inventors: Ahmad Mahdi Alshehri, Riyadh (SA); Mohammed Sabri Abdelghani, Riyadh (SA); Ahmed Alzenaidi, Riyadh (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 125 days.

This patent is subject to a terminal disclaimer.

(21) Appl. No.: 17/760,103

(22) PCT Filed: Jan. 26, 2021

(86) PCT No.: PCT/IB2021/050591
§ 371 (c)(1),
(2) Date: Aug. 4, 2022

(87) PCT Pub. No.: WO2021/156707
PCT Pub. Date: Aug. 12, 2021

(65) Prior Publication Data
US 2023/0064093 A1 Mar. 2, 2023

Related U.S. Application Data

(60) Provisional application No. 62/971,163, filed on Feb. 6, 2020.

(51) Int. Cl.
*B01D 3/40* (2006.01)
*B01D 3/14* (2006.01)
(Continued)

(52) U.S. Cl.
CPC ........... *C07C 7/08* (2013.01); *B01D 3/143* (2013.01); *B01D 3/322* (2013.01); *B01D 3/40* (2013.01);
(Continued)

(58) Field of Classification Search
CPC .... C07C 7/04; C07C 7/05; C07C 7/06; C07C 7/08; C07C 9/10; C07C 9/12;
(Continued)

(56) References Cited

U.S. PATENT DOCUMENTS 2,744,394 A * 5/1956 Newton ............... C07C 7/05
62/635
3,338,799 A * 8/1967 Brandt .................. B01D 3/40
203/84

(Continued)

FOREIGN PATENT DOCUMENTS

CN 1298375 A 6/2001
CN 103304359 A 9/2013
(Continued)

OTHER PUBLICATIONS

Norbert Asprion, Gerd Kaibel, Dividing wall colums: Fundamentals and recent advances, Chemical Engineering and Processing: Process Intensification, vol. 49, Issue 2, 2010, pp. 139-146, ISSN 0255-2701, https://doi.org/10.1016/j.cep.2010.01.013.*
(Continued)

*Primary Examiner* — Jonathan Luke Pilcher
(74) *Attorney, Agent, or Firm* — Norton Rose Fulbright US LLP

(57) ABSTRACT

A system and a method for separating $C_4$ and recovering 1,3-butadiene are disclosed. The system includes a main washer column, a rectifier column for separating a bottom stream from the main washer column, an after washer column for purifying 1,3-butadiene from a side stream of the
(Continued)

rectifier column comprising acetylenes and butadienes, a degasser column for separating a bottom stream from the rectifier column to produce a lean solvent stream. The lean solvent stream comprises primarily the solvent and about 8.3% water used in the main washer column and after washer column. A reboiler for the rectifier column includes one or more heat exchange units. At least one of the heat exchange units of the reboiler for the rectifier column uses steam as heating medium.

17 Claims, 4 Drawing Sheets

(51) Int. Cl.
*B01D 3/32* (2006.01)
*C07C 7/00* (2006.01)
*C07C 7/08* (2006.01)
*C07C 9/10* (2006.01)
*C07C 11/08* (2006.01)
*C07C 11/167* (2006.01)
*C07C 11/22* (2006.01)
*C07C 11/24* (2006.01)

(52) U.S. Cl.
CPC ............... *C07C 7/005* (2013.01); *C07C 9/10* (2013.01); *C07C 11/08* (2013.01); *C07C 11/167* (2013.01); *C07C 11/22* (2013.01); *C07C 11/24* (2013.01)

(58) Field of Classification Search
CPC ......... C07C 11/08; C07C 11/09; C07C 11/16; C07C 11/167; C07C 11/22; C07C 11/24; B01D 3/141; B01D 3/143; B01D 3/322; B01D 3/40
See application file for complete search history.

(56) References Cited

U.S. PATENT DOCUMENTS

| | | | |
|---|---|---|---|
| 6,337,429 | B1 | 1/2002 | Kindler et al. |
| 9,296,667 | B2 * | 3/2016 | Schwint ............. B01D 19/0068 |
| 9,409,838 | B2 * | 8/2016 | Schwint ................. C07C 7/005 |
| 9,611,195 | B2 * | 4/2017 | Brummer ................... C07C 7/10 |
| 9,656,929 | B2 * | 5/2017 | Abdelghani ............. C07C 7/005 |
| 9,744,475 | B2 | 8/2017 | Schwint et al. |
| 10,569,192 | B2 * | 2/2020 | Asprion ................. B01D 3/326 |
| 11,780,789 | B2 * | 10/2023 | Abdelghani ............. C07C 7/005 |
| | | | 585/809 |
| 2014/0100405 | A1 * | 4/2014 | Brummer ................ C07C 7/005 |
| | | | 202/168 |
| 2014/0121437 | A1 * | 5/2014 | Schwint ............. B01D 19/0068 |
| | | | 202/168 |
| 2014/0124358 | A1 * | 5/2014 | Schwint .................... C07C 7/08 |
| | | | 202/168 |
| 2016/0122265 | A1 * | 5/2016 | Abdelghani ........... B01D 3/143 |
| | | | 585/810 |
| 2018/0327337 | A1 | 11/2018 | Senetar et al. |
| 2019/0031581 | A1 | 1/2019 | Asprion |

FOREIGN PATENT DOCUMENTS

| | | |
|---|---|---|
| CN | 104812725 A | 7/2015 |
| CN | 104837796 A | 8/2015 |
| EP | 3194349 A1 | 7/2017 |
| EP | 3390330 A1 | 10/2018 |
| KR | 101789892 B1 | 11/2017 |
| KR | 20180104640 A | 9/2018 |
| SA | 99200254 B1 | 7/2006 |
| WO | WO2014058585 A1 | 4/2014 |
| WO | WO2017103776 A1 | 6/2017 |

OTHER PUBLICATIONS

International Search Report and Written Opinion from PCT/IB2021/050591 dated Apr. 26, 2021, 11 pages.

* cited by examiner

SYSTEMS AND METHODS FOR ENHANCING THE EXTRACTIVE SECTION OPERABILITY AND MODIFYING SOLVENT HEAT RECOVERY CYCLE IN THE SEPARATION OF C4 MIXTURES

CROSS REFERENCE TO RELATED APPLICATIONS

This application is a national phase application under 35 U.S.C. § 371 of International Application No. PCT/IB2021/050591 filed Jan. 26, 2021, which claims priority to U.S. Provisional Patent Application No. 62/971,163 filed Feb. 6, 2020. The entire contents of each of the above-referenced disclosures is specifically incorporated by reference herein without disclaimer.

FIELD OF INVENTION

The present invention generally relates to systems and methods for separating $C_4$ hydrocarbons. More specifically, the present invention relates to systems and methods for separating 1,3-butadiene from a $C_4$ mixture with an optimized heat recovery cycle.

BACKGROUND OF THE INVENTION 1,3-butadiene is a valuable chemical that can be used as a raw material in many chemical production processes. For instance, 1,3-butadiene can be used to produce polybutadiene, which is the main component of synthetic rubber. Furthermore, butadiene can be used for making adiponitrile, a nylon intermediate, via a hydrocyanation process.

Conventionally, 1,3-butadiene is produced via various processes including extraction from $C_4$ raffinate of steam crackers, dehydrogenation of n-butane, and dehydrogenation of butenes. In the process of extractive distillation of $C_4$ raffinate from steam crackers, a 1,3-butadiene containing stream from an extractive distillation column is separated in a rectifier column to further separate the solvent and 1,3-butadiene. The solvent is further purified in a degasser column to produce purified solvent. The solvent from the degasser column is used as the heating medium for a reboiler for the rectifier column, which includes multiple heat exchangers in series, for sufficient heat recovery. However, the reliability and stability of the conventional system can be an issue that affects the 1,3-butadiene production due to high sensitivity of the heat exchanger performance to changes in the purified solvent stream. Furthermore, the heat exchangers of the reboiler are highly susceptible to fouling, which can cause system instabilities for 1,3-butadiene production.

Overall, while systems and methods for separating 1,3-butadiene from a $C_4$ mixture exist, the need for improvements in this field persists in light of at least the aforementioned drawbacks for the conventional systems and methods.

BRIEF SUMMARY OF THE INVENTION

A solution to at least the above-mentioned problem associated with the systems and methods for separating 1,3-butadiene from a $C_4$ hydrocarbon mixture has been discovered. The solution resides in a system and a method for separating a $C_4$ hydrocarbon mixture and recovering 1,3-butadiene. The method includes subjecting the $C_4$ hydrocarbon mixture to extractive distillation, separating a bottom stream from the extractive distillation column in a rectifier column, and purifying solvent in a degasser unit. Notably, the reboiler for the rectifier column can include two or more heat exchangers in series with the last of the heat exchangers in series using steam as heating medium. This can be beneficial for at least enabling the heating performance of the reboiler to be manipulated independently from any process streams of the system, therefore increasing the stability and reliability for the system. Additionally, the first one or more exchangers of the rectifier column reboiler can use purified solvent stream from the degasser column as heating medium, resulting in optimized heat integration of the system. Moreover, the extra heat provided to the system by the steam can be further recovered in the downstream operation units, further optimizing the heat recovery and maintaining heat balance for the system. Therefore, the system and methods of the present invention provide a technical solution to at least some of the problems associated with the conventional systems and methods mentioned above.

Embodiments of the invention include a method of separating a mixture of $C_4$ hydrocarbons and a solvent. The method comprises separating the mixture in a rectifier column to produce a top stream comprising at least some $C_4$ hydrocarbons and a bottom stream comprising (a) primarily the solvent and (b) some $C_4$ hydrocarbons. The method comprises separating the bottom stream in a degasser column to produce a lean solvent stream comprising primarily the solvent. A reboiler for the rectifier column comprises one or more heat exchange units in series and at least one of the heat exchange units uses steam as a heating medium.

Embodiments of the invention include a method of separating a mixture of $C_4$ hydrocarbons and a solvent. The method comprises separating the mixture in a rectifier column to produce a top stream comprising at least some $C_4$ hydrocarbons and a bottom stream comprising (a) primarily the solvent and (b) some $C_4$ hydrocarbons. The method comprises separating the bottom stream in a degasser column to produce a lean solvent stream comprising primarily the solvent. A reboiler for the rectifier column comprises two or more heat exchange units in series. The last heat exchange unit in series uses steam as a heating medium, and the heat exchange units upstream of the last heat exchange unit use the lean solvent stream as a heating medium.

Embodiments of the invention include a method of separating 1,3-butadiene from a $C_4$ hydrocarbon feed stream. The method comprises separating, in a main washer column, the $C_4$ hydrocarbon feed stream via extractive distillation to produce (i) a first overhead stream comprising 1-butene, 2-butene, isobutylene, isobutane, n-butane, or combinations thereof, and (ii) a first bottom stream comprising a $C_4$ hydrocarbon mixture comprising primarily 1,3-butadiene, a solvent, and $C_4$ hydrocarbons other than 1,3-butadiene, collectively. The method comprises separating the first bottom stream in a rectifier column to produce (a) a top stream comprising at least some of the $C_4$ hydrocarbons other than 1,3-butadiene, (b) a first side stream comprising 1,3-butadiene and the solvent, and (c) a bottom stream comprising primarily the solvent and at least some $C_4$ hydrocarbons. A reboiler for the rectifier column comprises two or more heat exchange units in series configured to heat the reboiler. The method comprises separating the first side stream in an after washer column to produce a crude 1,3-butadiene stream comprising primarily 1,3-butadiene. The method comprises separating the bottom stream in a degasser column to produce a lean solvent stream comprising primarily the solvent. The method comprises flowing the lean solvent stream to at least one of the heat exchange units as a heating medium for the reboiler for the rectifier column to produce a first cooled lean solvent stream. The method further comprises flowing a low pressure steam to the last heat exchange unit in series as a heating medium to heat fluid in the reboiler for the rectifier column to a pre-determined final temperature.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "lean solvent stream" as that term is used in the specification and/or claims, means a stream comprising no less than 91.7 wt. % a solvent, or no more than 8.7 wt. % hydrocarbons.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, 1,3-butadiene is separated in a system that includes an extractive distillation column, a rectifier column, and a degasser column where the purified solvent stream from the degasser column is used as heating medium for the reboiler for the rectifier column. The performance of the reboiler for the rectifier column is highly sensitive to any changes in the purified solvent stream, and the reboiler for the rectifier column is susceptible to fouling. Thus, maintaining stability and reliability of the separation performance in the rectifier column and the entire system is challenging. The present invention provides a solution to this problem. The solution is premised on a method of separating 1,3-butadiene from a $C_4$ hydrocarbon mixture that utilizes steam as heating medium of the last heat exchanger in series of the rectifier column reboiler. The parameters (e.g., temperature, and pressure) of the steam can be adjusted independently from any process streams in the system, and controlled based on the amount of heat needed to keep the reboiler in a desired temperature range and/or mitigating heat loss caused by fouling in heat exchangers that uses purified solvent as heating medium. Thus, the disclosed method is capable of increasing the stability and reliability of the 1,3-butadiene production system. Additionally, the extra heat provided by the steam used in the last heat exchanger can be further utilized in a downstream operation unit, for instance a propyne separation column, thus further enhancing the optimization of the heat cycle for the system. These and other non-limiting aspects of the present invention are discussed in further detail in the following sections.

A. System for Separating $C_4$ Hydrocarbons

Figure 1A:
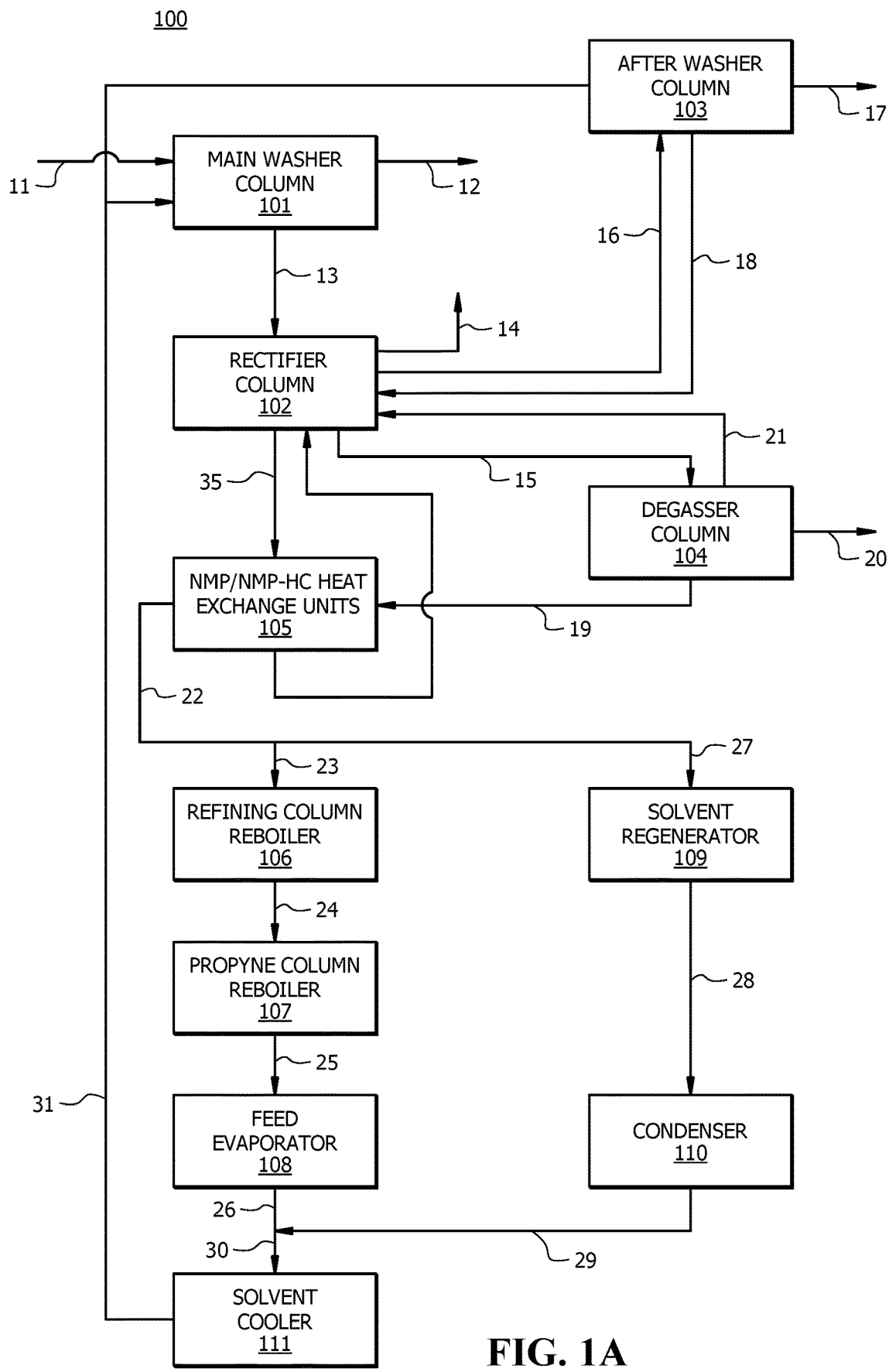
FIG. 1A shows a schematic diagram of a system for separating a $C_4$ hydrocarbon mixture, according to embodiments of the invention.

In embodiments of the invention, the system for separating $C_4$ hydrocarbons comprises a main washer column (e.g., extractive distillation column), a rectifier column, and a degasser column. The system is capable of increasing the reliability and stability for producing 1,3-butadiene. With reference to FIG. 1A, a schematic diagram is shown for system 100, which is used for separating $C_4$ hydrocarbons and producing 1,3-butadiene with improved system stability and reliability compared to conventional systems.

According to embodiments of the invention, system 100 comprises main washer column 101 configured to separate $C_4$ hydrocarbon feed stream 11 to produce first overhead stream 12 comprising 1-butene, 2-butene, isobutylene, isobutane, n-butane, or combinations thereof and first bottom stream 13 comprising a mixture of $C_4$ hydrocarbons and a solvent. In embodiments of the invention, main washer column 101 includes an extractive distillation column. In embodiments of the invention, the mixture of $C_4$ hydrocarbons of first bottom stream 13 comprises 1,3-butadiene. The mixture of $C_4$ hydrocarbons can further comprise $C_4$ hydrocarbons. The solvent comprises N-methyl-2-pyrrolidone (NMP). The solvent may further comprise 8-10 wt. % water, preferably about 8.3 wt. % water. The $C_4$ hydrocarbons may include 1-butene, 2-butene, n-butane, isobutane, isobutylene, or combinations thereof.

According to embodiments of the invention, a bottom outlet of main washer column 101 is in fluid communication with rectifier column 102 such that first bottom stream flows from main washer column 101 to rectifier column 102. In embodiments of the invention, rectifier column 102 is configured to separate first bottom stream 13 to form top stream 14 comprising at least some $C_4$ hydrocarbons and bottom stream 15 comprising primarily the solvent and some $C_4$ hydrocarbons. $C_4$ hydrocarbons in both top stream 14 and bottom stream 15 include $C_4$ hydrocarbons. In embodiments of the invention, rectifier column 102 can be configured to use 1,3-butadiene to strip butenes from the solvent into top stream 14. At least a portion of top stream 14 is recycled back to main washer column 101. Reboiler 105 for rectifier column 102 may include one or more heat exchange units configured to heat and boil bottom liquid stream 35 from rectifier column 102 to form bottom stream 15. In embodiments of the invention, rectifier column 102 is further configured to produce first side stream 16 comprising primarily 1,3-butadiene and acetylenes, collectively.

According to embodiments of the invention, a side outlet of rectifier column 102 is in fluid communication with after washer column 103 such that first side stream 16 flows from rectifier column 102 to after washer column 103. After washer column 103 may be configured to separate first side stream 16 to form crude butadiene stream 17 comprising primarily 1,3-butadiene and after washer bottom stream 18 comprising primarily the solvent and acetylenes. In embodiments of the invention, after washer column 103 includes a distillation column or an extractive distillation column. In embodiments of the invention, after washer column 103 is an extractive distillation column, which uses the lean solvent of solvent feed stream 31 to dissolve the acetylenes in stream 16 which is sent back to the rectifier column again via after washer bottom stream 18.

According to embodiments of the invention, a bottom outlet of rectifier column 102 is in fluid communication with degasser column 104 such that bottom stream 15 flows from rectifier column 102 to degasser column 104. In embodiments of the invention, degasser column 104 is configured to separate bottom stream 15 to form lean solvent stream 19 comprising the solvent, and second side stream 20 comprising acetylene. In embodiments of the invention, degasser column 104 is configured to further produce third overhead stream 21 comprising $C_4$ hydrocarbons. In embodiments of the invention, degasser column 104 may include a distillation column.

Figure 1B:
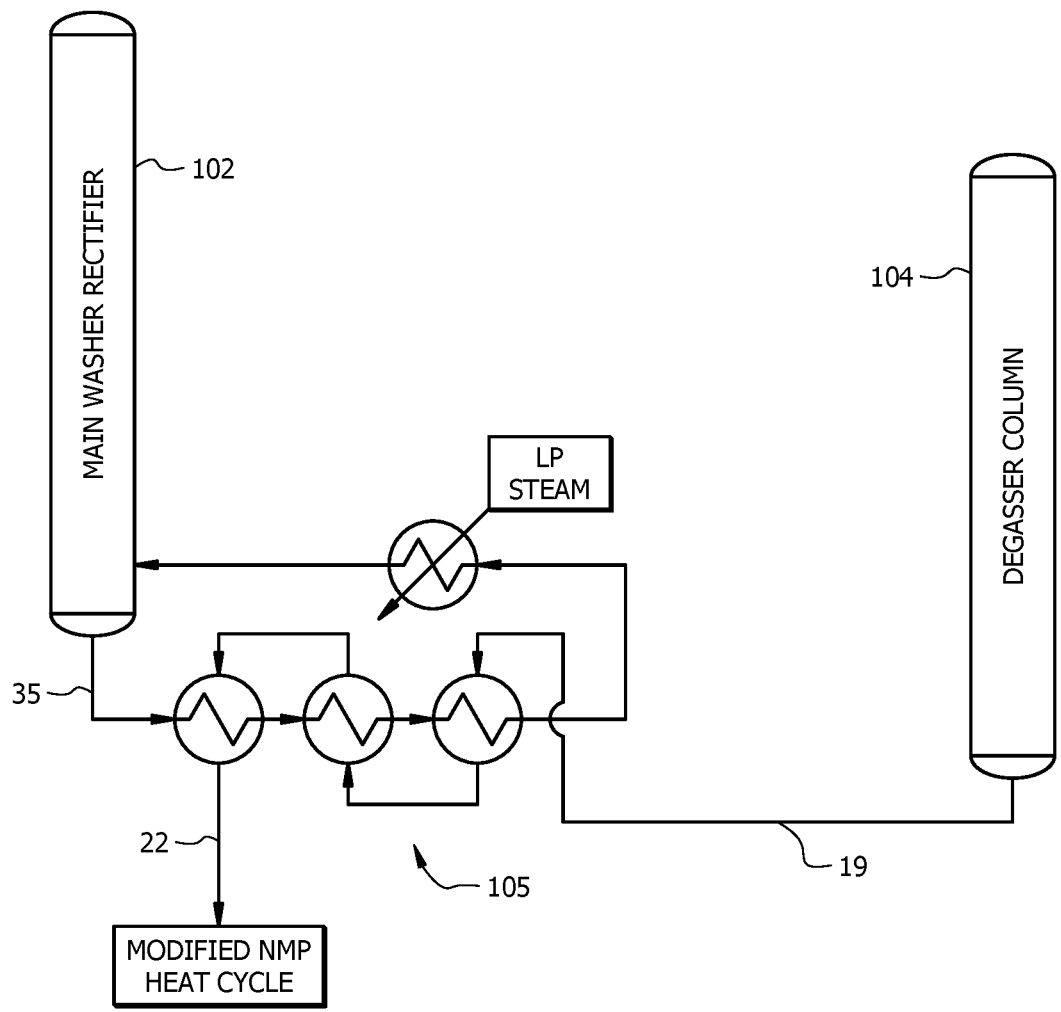
FIG. 1B shows a schematic diagram of a configuration of a rectifier column and a degasser column of a system for separating a $C_4$ hydrocarbon mixture, according to embodiments of the invention.

According to embodiments of the invention, a top outlet of degasser column 104 is in fluid communication with rectifier column 102 such that third overhead stream 21 flows from degasser column 104 to rectifier column 102. In embodiments of the invention, a bottom outlet of degasser column 104 is in fluid communication with reboiler 105 for rectifier column 102 such that lean solvent stream 19 flows through reboiler 105 as a heating medium to form first cooled lean solvent stream 22. As shown in FIG. 1B, reboiler 105 comprises two or more heat exchange units in series. The two or more heat exchange units can include heat exchangers in shell and tube configuration for counter-current heat exchange. At least the last one of the heat exchange units in series uses steam as a heating medium. The heat exchange units upstream of the last heat exchange unit may use lean solvent stream 19 as a heating medium to heat and boil bottom liquid stream 35 to form bottom stream 15 and first cooled lean solvent stream 22. In embodiments of the invention, reboiler 105 comprises four heat exchangers in series. The first three heat exchangers in series are configured to use lean solvent stream 19 as heating medium. The last heat exchanger in series, which is downstream to the first three heat exchangers, is configured to use steam as a heating medium. The steam used as heating medium for the last heat exchanger in series of reboiler 105 may be low pressure steam. The low pressure steam may be at a pressure of 3 to 4 bar. In embodiments of the invention, downstream of low pressure steam can be flowed to a condensate system of system 100. The condensate system can be configured to adjust temperature of the low pressure steam and/or redistribute the low pressure steam to one or more units that utilize the low pressure steam. According to embodiments of the invention, the condensate system of system 100 includes two drums comprising a medium pressure condensate drum for medium pressure steam and a low pressure condensate drum for low pressure steam.

According to embodiments of the invention, an outlet of reboiler 105 is in fluid communication with refining column 106 such that at least a portion of first cooled lean solvent stream 22, which forms downstream heating medium stream 23, flows from reboiler 105 to a reboiler of refining column 106 as a heating medium and forms a cooled downstream heating medium stream 24. In embodiments of the invention, refining column 106 is configured to purify 1,3-butadiene in crude butadiene stream 17. In embodiments of the invention, an outlet of the reboiler of refining column 106 is in fluid communication with a reboiler of propyne column 107 such that cooled downstream heating medium stream 24 flows through the reboiler of propyne column 107 as a heating medium to form second cooled heating medium stream 25. Propyne column 107 may be configured to separate purify 1,3-butadiene from the crude butadiene stream 17 by removing propyne as an overhead product.

According to embodiments of the invention, an outlet of the reboiler of propyne column 107 is in fluid communication with feed evaporator 108 such that second cooled heating medium stream 25 flows from the reboiler of propyne column 107 to feed evaporator 108 as a heating medium to form third cooled heating medium stream 26.

According to embodiments of the invention, an outlet of reboiler 105 for rectifier 102 is in fluid communication with solvent regenerator 109 such that at least a portion of first cooled lean solvent stream 22, which forms solvent regenerator feed stream 27, flows from reboiler 105 to solvent regenerator 109. Solvent regenerator 109 may be configured to regenerate the solvent of solvent regenerator feed stream 27 by physical separation under vacuum conditions to form regenerated solvent stream 28. In embodiments of the invention, system 100 may further comprise condenser 110 configured to condense regenerator solvent stream to form condensed solvent stream 29.

In embodiments of the invention, third cooled heating medium stream 26 is combined with condensed solvent stream 29 to form combined solvent stream 30. According to embodiments of the invention, system 100 includes solvent cooler 111 configured to cool combined solvent stream 30 to produce solvent feed stream 31. Solvent cooler 111 may include a shell and tube heat exchanger. At least a portion of solvent feed stream 31 may be fed into main washer column 101 and/or after washer column 103.

B. Method of Separating $C_4$ Hydrocarbons

Figure 2:
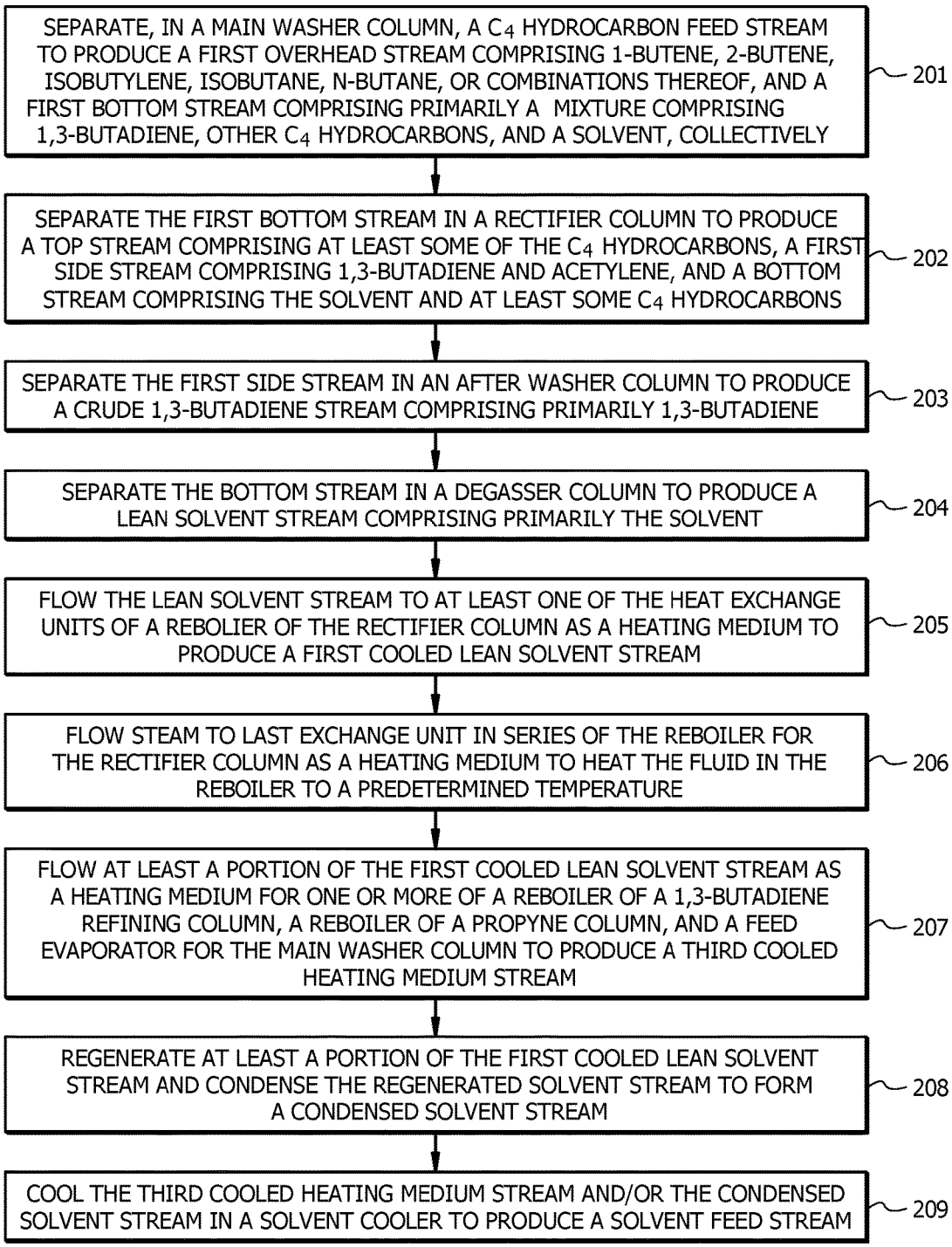
FIG. 2 shows a schematic flowchart of a method of for separating a $C_4$ hydrocarbon mixture, according to embodiments of the invention.

Methods for separating $C_4$ hydrocarbons and recovering 1,3-butadiene have been discovered. As shown in FIG. 2, embodiments of the invention include method 200 for separating $C_4$ hydrocarbons. Method 200 may be implemented by system 100, as shown in FIG. 1A and described above.

According to embodiments of the invention, as shown in block 201, method 200 comprises separating, in main washer column 101, $C_4$ hydrocarbon feed stream 11 to produce (i) first overhead stream 12 comprising 1-butene, 2-butene, isobutylene, isobutane, n-butane, or combinations thereof, and (ii) first bottom stream 13 comprising primarily a $C_4$ hydrocarbon mixture, and a solvent, collectively. In embodiments of the invention, the separating at block 201 is conducted via extractive distillation. The $C_4$ hydrocarbon mixture comprises 1,3-butadiene and other $C_4$ hydrocarbons including n-butane, isobutane, 1-butene, 2-butene, isobutylene, or combinations thereof. The $C_4$ hydrocarbon mixture may further include $C_4$ acetylenes and/or propyne. In embodiments of the invention, main washer column 101 is operated at an overhead temperature range of 40 to 45° C. In embodiments of the invention, main washer column 101 may not include a reboiler and the bottom product of first bottom stream 13 is diverted to the main washer rectifier column directly. Main washer column 101 may be operated at an operating pressure in a range of 4 to 5 bar and all ranges and values there between including 4 to 4.1 bar, 4.1 to 4.2 bar, 4.2 to 4.3 bar, 4.3 to 4.4 bar, 4.4 to 4.5 bar, 4.5 to 4.6 bar, 4.6 to 4.7 bar, 4.7 to 4.8 bar, 4.8 to 4.9 bar, and 4.9 to 5.0 bar. The $C_4$ hydrocarbons other than 1,3-butadiene comprise 1-butene, 2-butene, n-butane, isobutane, isobutylene, or combinations thereof. First overhead stream 12, in embodiments of the invention, can include 0.2 wt. % to 1.0 wt. %. 1,3-butadiene and all ranges and values there between including ranges of 0.2 to 0.3 wt. %, 0.3 to 0.4 wt. %, 0.4 to 0.5 wt. %, 0.5 to 0.6 wt. %, 0.6 to 0.7 wt. %, 0.7 to 0.8 wt. %, 0.8 to 0.9 wt. %, and 0.9 to 1.0 wt. %.

According to embodiments of the invention, as shown in block 202, method 200 comprises separating first bottom stream 13 comprising the $C_4$ hydrocarbon mixture by rectifier column 102 to produce top stream 14 comprising at least some of the $C_4$ hydrocarbons, first side stream 16 comprising 1,3-butadiene and acetylenes, and bottom stream 15 comprising primarily the solvent and at least some $C_4$ hydrocarbons. Bottom stream 15 may include 5 to 10 wt. % hydrocarbons. In embodiments of the invention, rectifier column 102 is operated at an overhead boiling temperature range of 55 to 75° C., and a reboiler temperature range of 100 to 125° C. Rectifier column 102 may be operated at an operating pressure of 4.5 to 5.5 bara and all ranges and values there between including ranges of 4.5 to 4.6 bara, 4.6 to 4.7 bara, 4.7 to 4.8 bara, 4.8 to 4.9 bara, 4.9 to 5.0 bara, 5.0 to 5.1 bara, 5.1 to 5.2 bara, 5.2 to 5.3 bara, 5.3 to 5.4 bara, and 5.4 to 5.5 bara. In embodiments of the invention, first side stream 16 comprises 96 to 99 wt. % 1,3-butadiene. First side stream 16 may be withdrawn from a first bottom quarter of rectifier column 102.

According to embodiments of the invention, as shown in block 203, method 200 includes separating first side stream 16 in after washer column 103 to produce crude butadiene stream 17 comprising primarily 1,3-butadiene. The separating at block 203 may be conducted via extractive distillation. In embodiments of the invention, crude butadiene stream 17 comprises 97 to 99 wt. % 1,3-butadiene. In embodiments of the invention, after washer column 103 is operated at an overhead boiling temperature range of 40 to 48° C. After washer column 103 maybe operated without a reboiler. In embodiments of the invention, after washer column 103 may be operated at an operating pressure of 4.5 to 5.5 bara. In embodiments of the invention, separating at block 203 further produces after washer bottom stream 18 comprising the solvent, and about 15 to 20 wt. % hydrocarbons. After washer bottom stream 18 may be flowed back to rectifier column 102. Crude butadiene stream 17 may be processed to propyne column 107 to remove propyne, and then flowed into refining column 106 for purifying 1,3-butadiene by removing heavies and 1,2-butadiene.

According to embodiments of the invention, as shown in block 204, method 200 includes separating bottom stream 15 in degasser column 104 to produce lean solvent stream 19 comprising primarily the solvent. Lean solvent stream 19 may comprise less than 1 wt. % hydrocarbons. In embodiments of the invention, separating at block 204 further produces third overhead stream 21 comprising $C_4$ hydrocarbons and/or second side stream 20 comprising acetylene. In embodiments of the invention, degasser column 104 is operated at an overhead boiling temperature range of 85 to 100° C., a reboiler temperature range of 145 to 155° C. In embodiments of the invention, lean solvent stream 19 comprises 91 to 93 wt. % of the solvent. Third overhead stream 21 may be flowed back to rectifier column 102. Second side stream 20 may be flowed to an acetylene column for recovering acetylene.

According to embodiments of the invention, as shown in block 205, method 200 includes flowing lean solvent stream 19 to at least one of the heat exchange units of reboiler 105 for rectifier column 102 as a heating medium to produce first cooled lean solvent stream 22. In embodiments of the invention, reboiler 105 comprises four heat exchange units in series and lean solvent stream 19 flows through the first three heat exchange units sequentially as the heating medium. In embodiments of the invention, the first cooled lean solvent stream 22 is at a temperature of 110 to 120° C. and all ranges and values there between including 110 to 111° C., 111 to 112° C., 112 to 113° C., 113 to 114° C., 114 to 115° C., 115 to 116° C., 116 to 117° C., 117 to 118° C., 118 to 119° C., 119 to 120° C. In embodiments of the invention, a volumetric flow rate ratio of lean solvent stream 19 to fluid being heated in reboiler 105 may be in a range of 0.5 to 2 and all ranges and values there between including ranges of 0.5 to 0.7, 0.7 to 0.8, 0.8 to 1.0, 1.0 to 1.2, 1.2 to 1.4, 1.4 to 1.6, 1.6 to 1.8, and 1.8 to 2.0.

According to embodiments of the invention, as shown in block 206, method 200 includes flowing steam to the last heat exchange unit in series of reboiler 105 as a heating medium to heat the fluid in reboiler 105 of rectifier column 102 to a pre-determined final temperature. In embodiments of the invention, the steam used in block 206 is low pressure steam at a pressure of 3 to 4 bara. The pre-determined final temperature may be in a range of 100 to 125° C. In embodiments of the invention, the steam used at block 206 is at a temperature of 130 to 135° C. The parameters including temperature, flow rate, and/or pressure of the steam used at block 206 can be adjusted to facilitate heating the fluid in reboiler 105 to the final pre-determined temperature. The flowing steps at blocks 205 and 206 may be capable of lowering shell side temperature of reboiler 105, thereby reducing fouling tendency in heat exchange units of reboiler 105.

According to embodiments of the invention, as shown in block 207, method 200 includes flowing at least a portion of first cooled lean solvent stream 22 as heating medium for one or more downstream units, including a reboiler of refining column 106, a reboiler of propyne column 107, and feed evaporator 108 of main washer column 101. to produce third cooled heating medium stream 26. In embodiments of the invention, at least a portion of first cooled lean solvent stream 22 is flowed as heating medium sequentially through a reboiler of refining column 106, a reboiler of propyne column 107, and feed evaporator 108 of main washer column 101. Third cooled heating medium stream 26 may be at a temperature of 70 to 75° C. Flowing at block 207 may be capable of reducing or eliminating an amount of hot condensate needed for heating the reboiler of propyne column 107.

According to embodiments of the invention, as shown in block 208, method 200 includes regenerating at least a portion of first cooled lean solvent stream 22 and condensing the regenerated solvent stream 28 to form condensed solvent stream 29. Condensed solvent stream 29 may be at a temperature of 45 to 55° C. According to embodiments of the invention, as shown in block 209, method 200 includes cooling third cooled heating medium stream 26 and/or condensed solvent stream 29 in solvent cooler 111 to produce solvent feed stream 31. Solvent feed stream 31 may be at a temperature of 36 to 44° C. and all ranges and values there between. At least a portion of solvent feed stream 31 may be fed into main washer column 101 and/or after washer column 103.

Although embodiments of the present invention have been described with reference to blocks of FIG. 2 should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

As part of the disclosure of the present invention, specific examples are included below. The examples are for illustrative purposes only and are not intended to limit the invention. Those of ordinary skill in the art will readily recognize parameters that can be changed or modified to yield essentially the same results.

Example

Comparison of Methods for Separating $C_4$ Hydrocarbons Via Simulation

Figure 3:
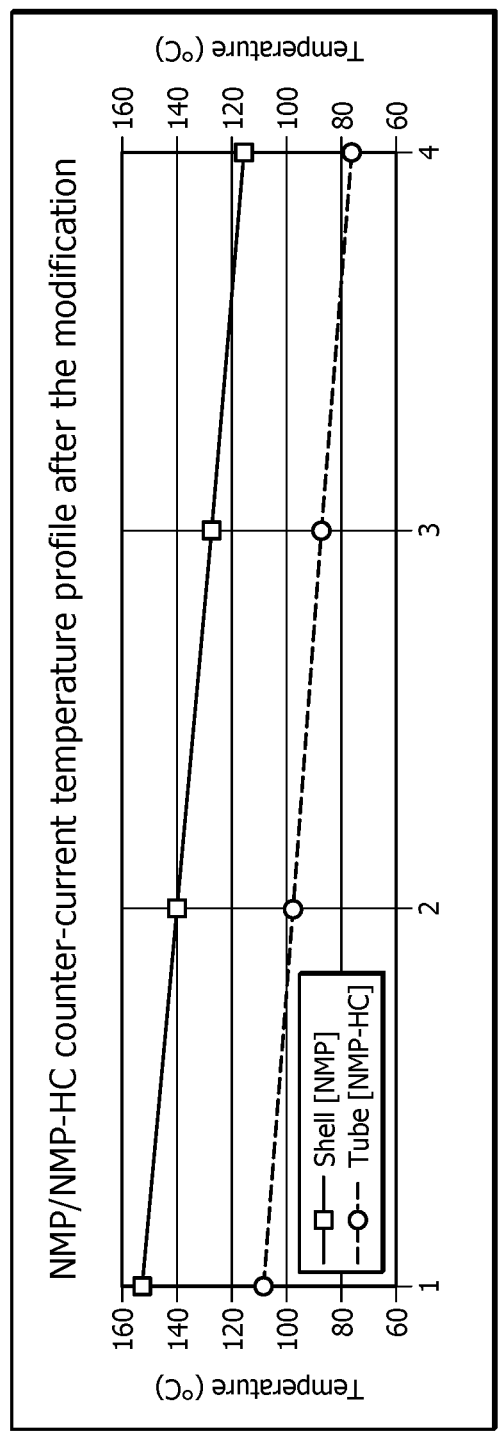
FIG. 3 shows a temperature profile for heat exchangers of a reboiler for a rectifier column in a system for separating a $C_4$ hydrocarbon mixture obtained by simulation.

Simulations based on a conventional process and the disclosed process for separating $C_4$ hydrocarbons and producing 1,3-butadiene were run in PRO II platform. The NMP cycle duty, which is the energy exchanged within the NMP cycle in the system, and utility consumption for both the conventional method (based case) and the disclosed method (post modification) were calculated. The results are shown in Table 1 and Table 2, respectively. The temperature profile of shell side and tube side of the three heat exchangers, which used lean solvent stream as heating medium, are plotted in FIG. 3.

TABLE 1

Comparison of NMP cycle duty
NMP Cycle Duty ( Base case 197 KTA)

| | Duty[MM kcal/hr] | |
|---|---|---|
| Exchanger | Base Case | Post modification |
| NMP/NMP-HC | 12.70 [4 exchangers] | 9.37 [3 exchangers] |
| Refining reboiler | 7.50 | 7.50 |
| Feed evaporator | 3.70 | 3.97 |
| Propyne reboiler | N/A | 2.27 |
| Solvent cooler | 2.78 | 3.78 |
| $T_{i, NMP}$ ° C. | | 151.4 |
| $T_{f, NMP}$ ° C. | | 38 |
| Total NMP duty | 26.68 | 26.86 |

* $T_{i\ NMP}$ means the solvent temperature at the beginning of the solvent cycle. In FIG. 1A, it is stream 19.
$Tf_{NMP}$ means the inlet solvent temperature at the end of the solvent cycle. In FIG. 1A, it is stream 31.

TABLE 2

Comparison of utility consumptions

| | Consumption [ton/ton BD] | |
|---|---|---|
| Type | Base Case | Post modification |
| MP steam | 1.40 | 1.40 |
| LP steam | 0.14 | 0.46 |
| Cond. | 3.63 | 0.08* |
| CW | 25.49 | 25.49 |

*MP means medium pressure steam (10-11 bara and 258-268° C.), LP means low pressure steam (3-4 bara and 142-147° C.), CW means cooling water (25-30° C.).

The results show that the disclosed method was capable of maintaining a comparable heat cycle duty as the conventional method. The disclosed method was capable of substantially eliminating the use of hot condensate, which is condensed low pressure steam at a temperature of 90 to 95° C., for heating the reboiler of propyne column.

In the context of the present invention, at the least the following 18 embodiments are described. Embodiment 1 is a method of separating a mixture of $C_4$ hydrocarbons and a solvent. The method includes separating the mixture of $C_4$ hydrocarbons in a rectifier column to produce a top stream containing at least some $C_4$ hydrocarbons and a bottom stream containing (a) primarily the solvent and (b) some $C_4$ hydrocarbons. The method further includes separating the bottom stream in a degasser column to produce a lean solvent stream containing primarily the solvent, wherein a reboiler for the rectifier column includes one or more heat exchange units in series and at least one of the heat exchange units uses steam as a heating medium. Embodiment 2 is the method of embodiment 1, wherein the reboiler for the rectifier column includes two or more heat exchange units in series, wherein a last heat exchange unit in series uses steam as a heating medium, and the heat exchange units upstream of the last heat exchange unit use the lean solvent stream as a heating medium. Embodiment 3 is the method of either of embodiments 1 or 2, wherein the mixture of $C_4$ hydrocarbons and the solvent is produced by a step of separating, in a main washer column, a $C_4$ hydrocarbon feed stream via extractive distillation to produce (i) a first overhead stream containing 1-butene, 2-butene, isobutylene, isobutane, n-butane, or combinations thereof, and (ii) the mixture of $C_4$ hydrocarbons and the solvent containing primarily 1,3-butadiene, the solvent, $C_4$ hydrocarbons other than 1,3-butadiene, collectively. Embodiment 4 is the method of any of embodiments 1 to 3, wherein the separating of the mixture of $C_4$ hydrocarbons and the solvent further produces a first side stream containing 1,3-butadiene and the acetylenes. Embodiment 5 is the method of embodiment 4, further including separating the first side stream in an after washer column to produce a crude butadiene stream containing primarily 1,3-butadiene. Embodiment 6 is the method of any of embodiments 1 to 5, further including flowing the lean solvent stream to at least one of the heat exchange units as a heating medium for the reboiler for the rectifier column to produce a first cooled lean solvent stream. The method further includes flowing a low pressure steam to the last heat exchange unit in series as a heating medium to heat the reboiler for the rectifier column to a pre-determined final temperature. Embodiment 7 is the method of embodiment 6, wherein the separating of the bottom stream in the degasser column further produces a second side stream containing acetylene. Embodiment 8 is the method of embodiment 7, further including purifying the acetylene in an acetylene column. Embodiment 9 is the method of embodiment 8, wherein the first cooled lean solvent stream is further flowed as the heating medium to provide heat for one or more reboilers of the propyne column for purifying propyne from the crude butadiene stream, a refining column for purifying 1,3-butadiene from crude butadiene stream, and a feed evaporator for the main washer column. Embodiment 10 is the method of embodiment 9, wherein the first cooled lean solvent stream is sequentially flowed through the reboilers of the propyne column, the refining column, and a feed evaporator for vaporizing a hydrocarbons feed stream for the main washer column as the heating medium. Embodiment 11 is the method of any of embodiments 6 to 10, wherein the pre-determined final temperature of the reboiler for the rectifier column is in a range of 100 to 125° C. Embodiment 12 is the method of any of embodiments 1 to 11, wherein the separating of the bottom stream in the degasser column further produces a second overhead stream containing $C_4$ hydrocarbons. Embodiment 13 is the method of embodiment 12, wherein the second overhead stream is flowed back to the rectifier column. Embodiment 14 is the method of any of embodiments 1 to 13, wherein the $C_4$ hydrocarbons contain 1-butene, 2-butene, n-butane, isobutane, isobutylene, 1,3-butadiene, or combinations thereof. Embodiment 15 is the method of any of embodiments 1 to 14, wherein the solvent contains N-methyl-2-pyrrolidone and 8.3 wt. % water. Embodiment 16 is the method of any of embodiments 1 to 15, wherein the rectifier column is operated at an overhead boiling temperature range of 55 to 75° C., a reboiler temperature range of 100 to 125° C., and an operating pressure of 4.5 to 5.5 bara. Embodiment 17 is the method of any of embodiments 1 to 16, wherein the degasser column is operated at an overhead boiling temperature range of 85 to 100° C., a reboiler temperature range of 145 to 155° C. Embodiment 18 is the method of any of embodiments 1 to 17, wherein the rectifier column includes four heat exchangers in series, wherein the first three of the heat exchangers is operated with the lean solvent stream as the heating medium, and the last heat exchanger is operated with a low pressure steam as the heating medium.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of separating a mixture of $C_4$ hydrocarbons and a solvent, the method comprising:
   separating the mixture of $C_4$ hydrocarbons and the solvent in a rectifier column to produce a top stream comprising at least some $C_4$ hydrocarbons and a bottom stream comprising (a) primarily the solvent and (b) some $C_4$ hydrocarbons;
   separating the bottom stream in a degasser column to produce a lean solvent stream comprising primarily the solvent;
wherein a reboiler for the rectifier column comprises four or more heat exchangers in series, wherein at least three of the heat exchangers are operated using the lean solvent stream as a heating medium, and wherein a last heat exchanger of the four or more heat exchangers in series is operated using low pressure steam as a heating medium;
wherein the degasser column is operated at an overhead boiling temperature range of 85 to 100° C.; and
wherein the method further comprises steps of:
   flowing the lean solvent stream to at least one of the four or more heat exchangers as a heating medium for the reboiler to heat a rectifier feed stream to produce a first cooled lean solvent stream and a heated rectifier feed stream; and
   flowing the low pressure steam to the last heat exchanger of the four or more heat exchangers as a heating medium to heat the reboiler to heat the heated rectifier feed stream and produce a further heated rectifier feed stream.

2. The method of claim 1, wherein the mixture of $C_4$ hydrocarbons and the solvent is produced by a step of separating, in a main washer column, a $C_4$ hydrocarbon feed stream via extractive distillation to produce (i) a first overhead stream comprising 1-butene, 2-butene, isobutylene, isobutane, n-butane, or combinations thereof, and (ii) the mixture of $C_4$ hydrocarbons and the solvent comprising primarily a mixture of 1,3-butadiene, the solvent, and $C_4$ hydrocarbons other than 1,3-butadiene.

3. The method of claim 1, wherein the separating of the mixture of $C_4$ hydrocarbons and the solvent in the rectifier column further produces a first side stream comprising 1,3-butadiene and acetylenes.

4. The method of claim 3, further comprising separating the first side stream in an after washer column to produce a crude butadiene stream comprising primarily 1,3-butadiene.

5. The method of claim 1, wherein the separating of the bottom stream in the degasser column further produces a second side stream comprising acetylene.

6. The method of claim 5, further comprising separating the second side stream in an acetylene column to produce a purified acetylene stream.

7. The method claim 1, wherein the first cooled lean solvent stream is provided as a heating medium to one or more of: i) a reboiler of a propyne column for purifying propyne from the crude butadiene stream, ii) a reboiler of a refining column for purifying 1,3-butadiene from the crude butadiene stream, and/or iii) a feed evaporator for the main washer column.

8. The method of claim 7, wherein the first cooled lean solvent stream is provided as a heating medium to all of the reboiler of the propyne column, the reboiler of the refining column, and the feed evaporator for the main washer column, such the first cooled lean solvent stream flows through the reboiler of the propyne column, the reboiler of the refining column, and the feed evaporator for the main washer column in series.

9. The method of claim 1, wherein the temperature of the reboiler for the rectifier column is in a range of 100 to 125° C.

10. The method of claim 1, wherein the separating of the bottom stream in the degasser column further produces a second overhead stream comprising $C_4$ hydrocarbons.

11. The method of claim 10, wherein the second overhead stream is flowed to the rectifier column.

12. The method of claim 1, wherein the $C_4$ hydrocarbons in the mixture of $C_4$ hydrocarbons and the solvent comprise 1-butene, 2-butene, n-butane, isobutane, isobutylene, 1,3-butadiene, or combinations thereof.

13. The method of claim 1, wherein the solvent comprises N-methyl-2-pyrrolidone and 8.3 wt. % water.

14. The method of claim 1, wherein the rectifier column is operated at an overhead boiling temperature range of 55 to 75° C., a reboiler temperature range of 100 to 125° C., and an operating pressure of 4.5 to 5.5 bara.

15. The method of claim 1, wherein the degasser column is operated at a reboiler temperature range of 145 to 155° C.

16. The method of claim 2, wherein the degasser column is operated at a reboiler temperature range of 145 to 155° C.

17. A method of separating a mixture of $C_4$ hydrocarbons and a solvent, the method comprising: separating the mixture of $C_4$ hydrocarbons and the solvent in a rectifier column to produce a top stream comprising at least some $C_4$ hydrocarbons and a bottom stream comprising (a) primarily the solvent and (b) some $C_4$ hydrocarbons; separating the bottom stream in a degasser column to produce a lean solvent stream comprising primarily the solvent;
wherein a reboiler for the rectifier column comprises four or more heat exchangers, wherein at least three of the heat exchangers are operated using the lean solvent stream as a heating medium, and wherein a last heat exchanger of the four or more heat exchangers in series is operated using low pressure steam as a heating medium;
wherein the rectifier column is operated at an overhead boiling temperature range of 55 to 75° C.; and
wherein the method further comprises steps of:
flowing the lean solvent stream to at least one of the four or more heat exchangers as a heating medium for the reboiler to heat a rectifier feed stream to produce a first cooled lean solvent stream and a heated rectifier feed stream; and
flowing the low pressure steam to the last heat exchanger of the four or more heat exchangers as a heating medium to heat the reboiler to heat the heated rectifier feed stream and produce a further heated rectifier feed stream.

* * * * *